United States Patent [19]

Sugimoto

[11] 4,383,036

[45] May 10, 1983

[54] PROCESS FOR THE PRODUCTION OF HUMAN CHORIONIC GONADOTROPIN

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 290,863

[22] Filed: Aug. 7, 1981

[30] Foreign Application Priority Data

Aug. 23, 1980 [JP] Japan ................................ 55-116140

[51] Int. Cl.³ ...................... C12P 21/02; C12P 21/04; C12P 21/00
[52] U.S. Cl. ...................................... 435/70; 435/68; 435/71
[58] Field of Search ............................ 435/68, 70, 71

[56] References Cited

U.S. PATENT DOCUMENTS 4,288,546 9/1981 Narasimhan et al. ................ 435/70

Primary Examiner—Sam Rosen
Attorney, Agent, or Firm—Browdy and Neimark

[57] ABSTRACT

The present invention relates to a process for the production of human chorionic gonadotropin (hCG).

More precisely, the invention relates to a process for the mass production of hCG, comprising in vivo multiplication of human lymphoblastoid cells capable of producing hCG, and hCG production by the multiplied human lymphoblastoid cells.

The hCG production according to the invention is extremely higher, in terms of hCG production per cell, than that attained by conventional process using in vitro tissue culture; thus, hCG can be used in a sufficient amount in the prevention and treatment of human diseases.

11 Claims, No Drawings

PROCESS FOR THE PRODUCTION OF HUMAN CHORIONIC GONADOTROPIN

DETAILED DESCRIPTION OF THE INVENTION

The present invention relates to a process for the production of human chorionic gonadotropin (abbreviated hCG hereinafter).

The hCG is a hormone, secreted by human syncytiotrophoblast cells of chlorionic villi, which stimulates the secretion of androgen and progestron.

Although a process for the production of hCG, using tissue culture, is known [A. S. Rabson et al., J. Natl. Cancer Inst., Vol. 50, pp. 669-674 (1973)], the process can not realize mass production of low-cost hCG due to its very low cell multiplication and low hCG production per cell.

The present invention has investigated processes for the mass production of hCG. The efforts resulted in an unexpected finding that human lymphoblastoid cells capable of producing hCG multiply rapidly and exhibit an extremely higher hCG production per cell; thus, the cells are suitable for the production of hCG.

More precisely, the present invention relates to a process for the production of hCG, characterized in multiplying human lymphoblastoid cells capable of producing hCG by transplanting said cells to a non-human warm-blooded animal body, or alternatively multiplying said cells by allowing said cells to multiply with a device by which the nutrient body fluid of a non-human warm-blooded animal is supplied to said cells, and allowing the cells multiplied by either of the above multiplication procedures to release hCG.

The process according to the present invention, besides realizing a greater hCG production, requires no or much less nutrient medium containing expensive serum for cell multiplication, and renders the maintenance of the culture medium during the cell multiplication much easier than in the case of in vitro tissue culture. Particularly, any human lymphoblastoid cells capable of producing hCG can be muliplied easily while utilizing the nutrient body fluid supplied from a non-human warm-blooded animal by transplanting the cells to the animal body, or suspending the cells in a diffusion chamber devised to receive the nutrient body fluid, and feeding the animal in the usual way. Also, the process is characterized by stabler and higher cell multiplication, and higher hCG production per cell.

As to the human lymphoblastoid cells usable in the invention, any human lymphoblastoid cells can be used so far as they produce hCG and multiply in a non-human warm-blooded animal body. For example, as such cells usable in the present invention there may be used human lymphoblastoid cells in which there has been introduced the hCG production governing genes of the human syncytiotrophoblast cells of the chorionic villi, human chorioepithelioma cells, or human chromophobe adenoma cells of the pituitary gland which inherently produce hCG, or human lung carcinoma cells which produce ectopic hCG. These hCG production governing genes may be introduced by means of cell fusion using polyethylene glycol or Sendai virus, or by genetic recombination technique using DNA ligase, nuclease and DNA polymerase. Human lymphoblastoid cells capable of producing ectopic hCG are also feasible in the present invention. Since transplantation of the above mentioned human lymphoblastoid cells to the animal body results in the easily disaggregatable massive tumors, and said massive tumors are hardly contaminated with the host animal cells, the multiplied live human lymphoblastoid cells can be harvested easily.

As to the animals usable in the invention, any animals can be used according to the invention so far as the cells multiply therein. For example, poultry such as chicken or pigeon, or mammalians such as dog, cat, monkey, goat, pig, cow, horse, rabbit, guinea pig, rat, hamster, mouse or nude mouse are advantageously usable in the present invention. Since such cell transplantation elicits undesirable immunoreaction, the use of a newborn of infant animal, or those in the youngest possible stage, for example, egg, foetus or embryo, is desirable. In order to reduce the immunoreaction, prior to the cell transplantation, the animal may be treated to reduce the immunoreaction as much as possible with X-ray or $\gamma$-ray irradiation, about 200-600 rem, or injection of antiserum or immunosuppressive agent prepared according to conventional method. Since nude mouse, used as the non-human warm-blooded animal, exhibits weaker immunoreaction even when in its adulthood, conveniently, any human lymphoblastoid cells can be implanted and multiplied rapidly therein without such pretreatment.

Stabilized cell multiplication and enhancement of hCG production can both be carried out by repeated transplantation using combination(s) of different non-human warm-blooded animals; for example, the objectives are attainable first by implanting the human lymphoblastoid cells in hamster and multiplying therein, then by reimplanting in nude mouse. Further, the repeated transplantation may be carried out with animals of the same class or division as well as those of the same species or genus.

As to where the human lymphoblastoid cells are implantable, the cells can be implanted in any sites of the animal so far as the cells multiply therein; for example, in allantoic cavity, or intravenously, intraperitoneally, or subcutaneously.

Besides direct cell transplantation of the human lymphoblastoid cells to the animal body, any conventional human lymphoblastoid line capable of producing hCG can be multiplied while utilizing the nutrient body fluid supplied from the animal body by embedding, for example, intraperitoneally, in said animal body a conventional diffusion chamber, of any of various shapes and sizes, and equipped with a porous membrane filter, ultra filter or hollow fiber with pore sizes of about $10^{-7}$–$10^{-5}$ m in diameter which prevents contamination with host cells into the diffusion chamber and allows the animal to supply the cells with its nutrient body fluid. Additionally, the diffusion chamber can be designed, if necessary, so it could be placed, for example, on the host animal, and the body fluid allowed to circulate from the animal body into the chamber, to enable observation of the cell suspension in the chamber through transparent side window(s), equipped on the chamber wall(s), and to enable replacement and exchange with a fresh chamber; cell multiplication thereby increases to a further higher level over the period of the animal life without any sacrifice of the host animal. Furthermore, when such a diffusion chamber is used, since the multiplied human lymphoblastoid cells can be harvested easily and no immunoreaction is elicited due to the absence of direct contact of the human cells with the host animal cells, any non-human warm-blooded animal can be used as the host in the present invention without any pretreatment to reduce the immunoreaction.

Feeding of the host animal implanted with the human lymphoblastoid cells can be carried out easily by conventional methods even after the cell transplantation, and no special care is required.

Maximum cell multiplication is attained about 1–20 weeks, generally 1–5 weeks, after the cell transplantation.

According to the present invention, the number of the human lymphoblastoid cells obtained per host ranges from about $10^7$–$10^{12}$ or more. In other words, the number of the human lymphoblastoid cells implanted in the animal body increases about $10^2$–$10^7$-fold or more, or about $10^1$–$10^6$-fold or more than that attained by in vitro tissue culture method using nutrient medium; thus the, cells are conveniently usable for hCG production.

As to the method by which the human cells are allowed to release hCG, any method can be employed so far as the human lymphoblastoid cells obtained by the above mentioned procedure release hCG thereby. For example, the multiplied human lymphoblastoid cells, obtained by multiplying in ascite in suspension and harvesting from said ascite, or by extracting the massive tumor formed subcutaneously and harvesting after the disaggregation of said massive tumor, are suspended to give a cell concentration of about $10^4$ to $10^8$ cells per ml in a nutrient medium, kept at a temperature of about 20°–40° C., and then incubated at this temperature for an additional one to 50 hours to produce hCG. Incubation of the cells in the presence of one or more members of a group comprising amino acids such as leucine, lysine, arginine and cysteine; inorganic salts such as sodium chloride, potassium chloride, calcium chloride and magnesium sulfate; and hormones such as luteinizing hormone releasing hormone further augments the hCG production.

The hCG thus obtained can be collected easily by purification and separation techniques using conventional procedures such as salting-out, dialysis, filtration, centrifugation, concentration and lyophilization. If a further purified hCG preparation is desirable, a hCG preparation of the highest purity can be obtained by the above mentioned techniques in combination with other conventional procedures such as adsorption and desorption with ion exchange, gel filtration, affinity chromatography, isoelectric point fractionation and electrophoresis.

The hCG preparation thus obtained is usable advantageously alone or in combination with other one or more agents for injection, external, internal, or diagnostical administration in the prevention and treatment of human diseases.

The hCG production in the culture medium was determined by radio-immunoassay method as described in A. R. Midgley, Jr., Endocrinology, Vol. 79, pp. 10–18 (1966), and expressed by International Unit (IU).

Several embodiments of the invention are disclosed hereinafter.

EXAMPLE 1

Disaggregated human chorioepithelioma cells, obtained by extracting from a chorioepithelioma patient and mincing, and a human leukemic lymphoblastoid line Namalwa were suspended together in a vessel with a salt solution, containing 140 mM NaCl, 54 mM KCl, 1 mM $NaH_2PO_4$ and 2 mM $CaCl_2$, to give respective cell concentration of about $10^4$ cells per ml. The ice-chilled cell suspension was mixed with a preparation of the same salt solution containing UV-irradiation preinactivated Sendai virus, transferred into a 37° C. incubator about five minutes after the mixing, and stirred therein for 30 minutes to effect cell fusion, introducing the hCG producibility of the human chorioepithelioma cells into the human leukemic lymphoblastoid line. After cloning the hybridoma cell strain capable of producing hCG according to convention methods, the hybridoma cell strain was implanted intraperitoneally in adult nude mice which were then fed in the usual way for five weeks. The resulting massive tumors, about 15 g each, were extracted and disaggregated by mincing and suspending in a physiological saline solution containing trypsin. After washing the cells with Earle's 199 medium (pH 7.2), supplemented with 10 v/v % foetal bovine serum, the cells were resuspended to give a concentration of about $10^6$ cells per ml in a fresh preparation of the same medium which contained 30 mM L-arginine, and then incubated at 35° C. for 20 hours to produce hCG. Thereafter, the cells were ultrasonicated, and the hCG in the supernatant was determined. The hCG production was about 230 IU per ml cell suspension.

The control cells, obtained by implanting the human chorioepithelioma cells in nude mice, feeding the animals for five weeks, extracting the resulting massive tumors, about 15 g each, and disaggregating the massive tumors, were treated as above to produce hCG. The hCG production was only about 20 IU per ml cell suspension.

EXAMPLE 2

Disaggregated human chromophobe adenoma cells, obtained by extracting from a patient suffering from chromophobe adenoma of the pituitary gland and mincing, were fused similarly as in EXAMPLE 1 with a human leukemic lymphoblastoid line JBL, introducing the hCG producibility of the human chromophobe adenoma cells into the human leukemic lymphoblastoid line. After cloning the hybridoma cell strain capable of producing hCG according to conventional methods, the hybridoma cell strain was implanted subcutaneously in newborn hamsters which had been preinjected to reduce their immunoreaction with antiserum prepared with rabbit according to conventional methods, and the animals were fed in usual way for three weeks. The resulting massive tumors formed subcutaneously and about 10 g each were extracted and disaggregated by mincing and suspending in a physiological saline solution containing collagenase. After washing the cells with Eagle's minimal essential medium (pH 7.2), supplemented with 5 v/v % human serum, the cells were resuspended to give a cell concentration of about $10^5$ cells per ml in a fresh preparation of the same medium which contained 20 mM L-lysine and 10 mM magnesium sulfate, and incubated at 37° C. for 15 hours to produce hCG. The hCG production was about 450 IU per ml cell suspension.

The control cells, obtained by implanting the human chromophobe adenoma cells in newborn hamsters, feeding the animals in the usual way for three weeks, extracting the resulting subcutaneously formed massive tumors, about 3 g each, and disaggregating the massive tumors, were treated similarly as above to produce hCG. The hCG production was only about 15 IU per ml cell suspension.

EXAMPLE 3

Newborn rats were implanted intravenously with a human leukemic lymphoblastoid line BALL-1 wherein the hCG producibility of the human chorioepithelioma cells was introduced similarly as in EXAMPLE 1, and then fed in the usual way for four weeks. The resulting massive tumors, about 30 g each, were extracted and disaggregated. The obtained human lymphoblastoid cells were washed with RPMI 1640 medium (pH 7.4), supplemented with 10 v/v % foetal bovine serum, suspended to give a cell concentration of about $10^7$ cells per ml in a fresh preparation of the same medium which contained 30 mM L-arginine, and incubated at 30° C. for about 40 hours to produce hCG. The hCG production was about 870 IU per ml cell suspension.

The control cells, obtained by implanting the human chorioepithelioma cells in newborn rats, feeding the animals in the usual way for four weeks, extracting the resulting massive tumors, about 5 g each, and disaggregating the massive tumors, were treated similarly as above to produce hCG. The hCG production was only about 30 IU per ml cell suspension.

EXAMPLE 4

After about 400 rem X-ray irradiation of adult mice to reduce their immunoreaction, the animals were implanted subcutaneously with a human leukemic lymphoblastoid line NALL-1 wherein the hCG productivity of the human chromophobe adenoma cells was introduced similarly as in EXAMPLE 2, and then fed in the usual way for three weeks. The resulting massive tumors formed subcutaneously and about 15 g each were extracted, disaggregated and treated similarly as in EXAMPLE 2 to produce hCG. The hCG production was about 520 IU per ml cell suspension.

The control cells, obtained by implanting the human chromophobe adenoma cells in mice, feeding the animals in the usual way for three weeks, extracting the resulting massive tumors, about 5 g each, and disaggregating the massive tumors, were treated similarly as above to produce hCG. The hCG production was only about 20 IU per ml cell suspension.

EXAMPLE 5

A human leukemic lymphoblastoid line TALL-1 wherein the hCG producibility of the human chorioepithelioma cells was introduced similarly as in EXAMPLE 1 was suspended in physiological saline solution, and then transferred into a plastic cylindrical diffusion chamber, inner volume about 10 ml, and equipped with a membrane filter having a pore size of about $0.5\mu$ in diameter. The chamber was embedded intraperitoneally in an adult rat. The animal was fed in the usual way for four weeks, and the chamber was removed. The human cell density in the chamber was about $7\times10^8$ cells per ml which was about $10^2$-fold higher or more than that attained by in vitro cultivation using a $CO_2$ incubator. The cells thus obtained were treated similarly as in EXAMPLE 3 to produce hCG. The hCG production was about 750 IU per ml cell suspension.

The control cells, obtained by suspending the human chorioepithelioma cells in the diffusion chamber, embedding intraperitoneally the chamber in an adult rat, and feeding the animal for four weeks (the obtained cell density about $10^7$ cells per ml), were treated similarly as above to produce hCG. The hCG production was only about 20 IU per ml cell suspension.

EXAMPLE 6

A human leukemic lymphoblastoid line JBL wherein the hCG producibility of the human syncytiotrophoblast cells of chorionic villi was introduced similarly as in EXAMPLE 1 was implanted in allantoic cavities of embryonated eggs which had been preincubated at 37° C. for five days. After incubation of the eggs at this temperature for an additional one week, the multiplied human lymphoblastoid cells were harvested. The cells were treated similarly as in EXAMPLE 1 to produce hCG. The hCG production was about 210 IU per ml cell suspension.

In the control experiment wherein the human syncytiotrophoblast cells of chorionic villi were implanted similarly as above in allantoic cavities of embryonated eggs, no cell multiplication was noted.

What we claim is:

1. A process for producing human chorionic gonadotropin (hCG), which comprises:
    (1) implanting human lymphoblastoid cells capable of producing hCG into a non-human warm-blooded animal;
    feeding the animal to cause the human cells therein to multiply;
    extracting and disaggregating the resultant multiplied human cells formed in the animal;
    culturing the human cells in a nutrient medium for a period sufficient to accumulate a significant amount of hCG; and
    harvesting the accumulated hCG from the culture, or alternatively,
    (2) placing human lymphoblastoid cells capable of producing hCG in suspension in a diffusion chamber;
    embedding the chamber in or placing the chamber on a non-human warm-blooded animal in a manner such that the nutrient body fluid of the non-human warm-blooded animal is supplied to the cells within the chamber;
    feeding the animal to cause the human cells in the chamber to multiply;
    collecting the multiplied human cells from the chamber;
    culturing the human cells in a nutrient medium for a period sufficient to accumulate a significant amount of hCG; and
    harvesting the accumulated hCG from the culture.

2. A process as set forth in claim 1, wherein said human lymphoblastoid cells capable of producing hCG are hybridoma cells derived by cell fusion of an established human lymphoblastoid line with human cells capable of producing hCG.

3. A process as set forth in claim 2, wherein said human cells capable of producing hCG which are fused to the established human lymphoblastoid line are human syncytiotrophoblast cells of chorionic villi.

4. A process as set forth in claim 2, wherein said human cells capable of producing hCG which are fused to the established human lymphoblastoid line are human chorioepithelioma cells.

5. A process as set forth in claim 2, wherein said human cells capable of producing hCG which are fused to the established human lymphoblastoid line are human chromophobe cells of the pituitary gland.

6. A process as set forth in claim 1, wherein said non-human warm-blooded animal is a poultry or a mammalian.

7. A process as set forth in claim 1, wherein said culturing steps are carried out in the presence of one or more members of the group consisting of amino acids, inorganic salts, and hormones.

8. A process as set forth in claim 2, wherein said cell fusion is accomplished using Sendai virus or polyethylene glycol.

9. A process as set forth in claim 2, wherein said established human lymphoblastoid line is Namalwa, BALL-1, NALL-1, TALL-1, or JBL.

10. A process as set forth in claim 1, wherein said non-human warm-blooded animal is a chicken, pigeon, dog, cat, monkey, goat, pig, cow, horse, rabbit, guinea pig, rat, hamster, mouse or nude mouse.

11. A process as set forth in claim 1, wherein said culturing steps are carried out in the presence of one or more members selected from the group consisting of leucine, lysine, arginine, cysteine, sodium chloride, potassium chloride, calcium chloride, magnesium sulfate, and luteinizing hormone releasing hormone.

* * * * *